United States Patent [19]

Reid, Jr. et al.

[11] 4,057,059
[45] Nov. 8, 1977

[54] INTERMITTENT POSITIVE PRESSURE BREATHING DEVICE

[75] Inventors: Karl N. Reid, Jr., Stillwater, Okla.; James Burr Ross, Omaha, Nebr.; Beegamudre N. Murali, Stillwater, Okla.

[73] Assignee: Oklahoma State University, Stillwater, Okla.

[21] Appl. No.: 588,870

[22] Filed: July 29, 1975

[51] Int. Cl.$^2$ ............................................ A61M 16/00
[52] U.S. Cl. ................................................. 128/145.8
[58] Field of Search ............... 128/145.8, 145.6, 145.5, 128/188; 131/624.12, 624.14

[56] References Cited

U.S. PATENT DOCUMENTS

| | | | |
|---|---|---|---|
| 3,683,951 | 8/1972 | Beaumont | 137/81.5 |
| 3,754,550 | 8/1973 | Kipling | 128/145.8 |
| 3,905,362 | 9/1975 | Eyrick et al. | 128/145.6 |
| 3,905,363 | 9/1975 | Dudley | 128/145.8 |
| 3,910,270 | 10/1975 | Stewart | 128/145.8 |
| 3,916,889 | 11/1975 | Russell | 128/145.8 |

*Primary Examiner*—Robert W. Michell
*Assistant Examiner*—Henry J. Recla
*Attorney, Agent, or Firm*—Head, Johnson & Chafin

[57] ABSTRACT

A ventilator implemented completely with fluidic devices provides independent control of inhalation time, exhalation time and breathing gas flow rate. The basic fluidic system comprises a low frequency oscillator which in the form of a flip flop is controlled in its two stable states by means of independently controlled time delay relays. The output of the flip flop is amplified by a digital amplifier and operates an on-off valve which is used to direct breathing gas from the source to the patient. Independent control of the flow rate of the breathing gas is by means of a needle valve. With this basic fluidic system, there are seven other features of the apparatus. One is a maximum pressure control which on inhalation is responsive to the patient's breathing air pressure. The second feature is a sensitivity control, which during exhalation is responsive to the patient inspiratory effort. The third feature is a positive end exhalation pressure control. The fourth is an intermittent mandatory ventilation control which permits breathing rates as low as one breath per minute. The fifth feature is a manual control which allows the termination of the exhalation phase and initiation of the inhalation phase manually. The sixth feature is a sensor which is responsive to the breathing gas pressure at the patient. If the apparatus becomes detached from the patient, pressure cycling is modified and an alarm system sensitive to this pressure is activated. The seventh feature is a safety valve which allows the patient to breathe atmospheric air when the supply pressure of the source gas fails.

19 Claims, 2 Drawing Figures

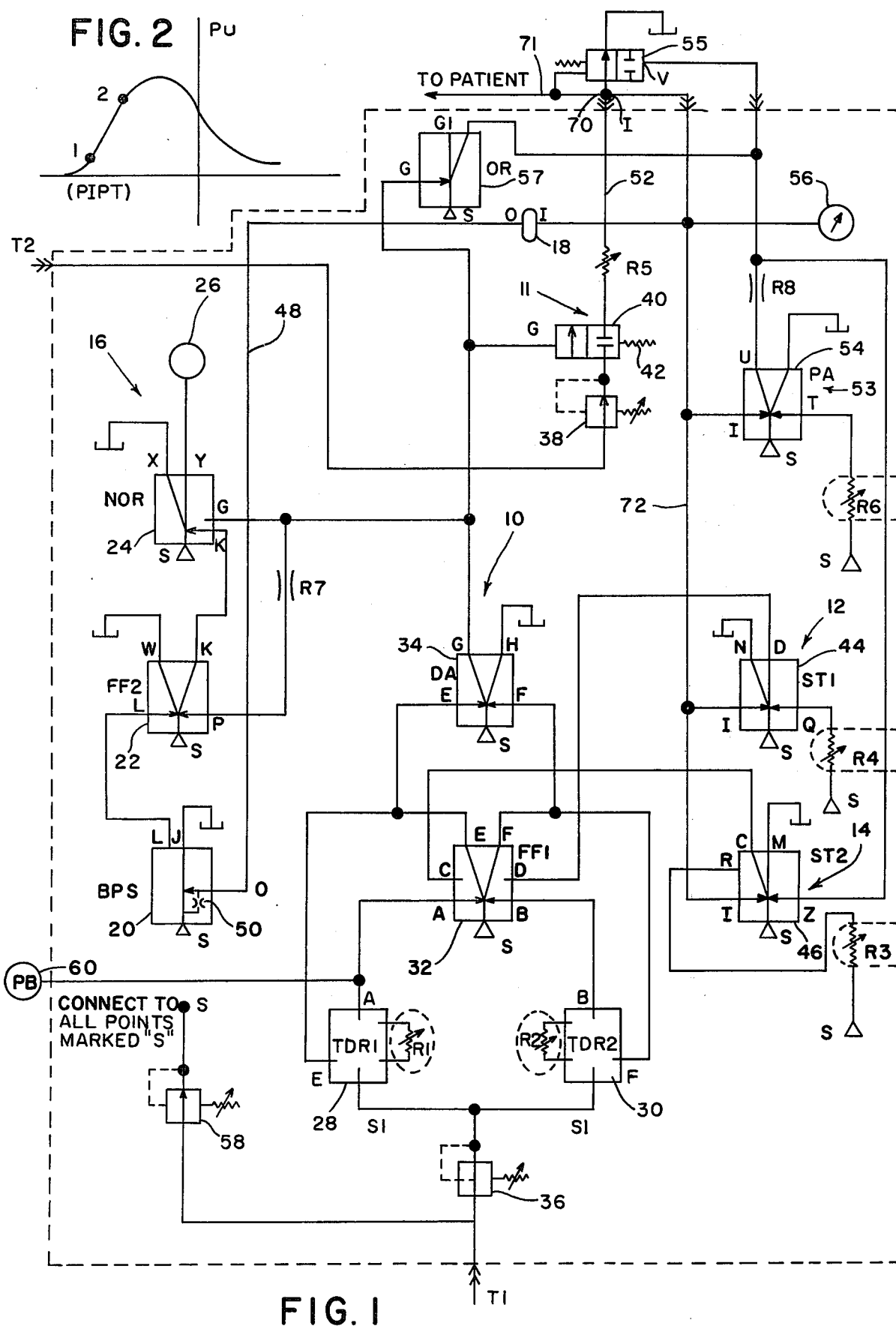

INTERMITTENT POSITIVE PRESSURE BREATHING DEVICE

BACKGROUND OF THE INVENTION

This invention lies in the field of breathing apparatus. More specifically, it is concerned with an automatic type of artificial ventilation or controlled respiration. It is called a ventilator which is used for controlled or assisted ventilation.

Most of the commonly used ventilators that are on the market today have one or more of the following drawbacks. First, their controls are interdependent, making it difficult for the physician to set the device to a desired condition. Second, the tidal volume delivered to the patient is a function of the respiratory parameters of the patient, hence constant readjustments of the controls are necessary as the respiratory parameters of the patient change. Also the prior art devices are constructed of electrical or electromechanical switches, relays, etc., which are subject to malfunction and failure; these devices are correspondingly difficult to maintain by hospital personnel.

It is a primary object of this invention to provide a reliable, simple ventilator that has independent control of the basic variables that may be required to be changed and to provide a number of safeguards to the patient.

SUMMARY OF THE INVENTION

This invention describes a ventilator which is capable of controlling or assisting ventilation. In the preferred embodiment, the ventilator is basically a time cycled, volume preset, maximum pressure limited device. However, due to the versatility of the basic circuit, and the independency of the basic controls, five different control options are available:

1. Independent control of inhalation time, exhalation time, and flow rate to the patient.
2. Independent control of inhalation time, exhalation time and tidal volume.
3. Independent control of inhalation time to exhalation time ratio, frequency of cycling, and flow rate.
4. Independent control of frequency of cycling and tidal volume.
5. Independent control of maximum pressure during inhalation at the patient's mouth, exhalation time, and flow rate.

The basic fluidic control circuit comprises a low frequency oscillator for timing the inhalation and exhalation phases, a digital amplifier for amplifying the output of the oscillator, and a two-way on-off valve for directing the breathing gas from the source to the patient. Along with the basic timing circuit, the control circuit of the ventilator includes seven other features:

1. A maximum pressure control which terminates the inhalation phase and initiates the exhalation phase when the patient pressure reaches a preset limit.
2. A sensitivity control which initiates an inhalation phase by terminating the exhalation phase when the patient inspiratory effort reaches a preset limit.
3. A positive end-exhalation pressure control which enables it to retain a positive pressure in the patient's lungs during the exhalation phase, without a significant "retard" effect.
4. An Intermittent Mandatory Ventilation (IMV) control which allows the patient's breathing rate to be reduced as low as one breath per minute.
5. A manual control which allows the inhalation phase to be initiated manually.
6. A disconnect alarm which gives a visual and/or audible signal when the apparatus is disconnected from the patient, or when a significant leak occurs in the breathing circuit.
7. A non-rebreathing valve which allows the patient to breathe atmospheric air when the supply pressure of the source gas fails, or anytime during the exhalation phase providing the patient's inspiratory effort is insufficient to initiate the inhalation phase.

In the preferred embodiment, a constant mass flow rate generator is connected to the patient during the inhalation phase. If the inhalation time control and the flow rate control are fixed, a given tidal volume will be delivered independent of patient condition (i.e., airway resistance and lung compliance), as long as the inhalation phase is not pressure limited. The change-over from inhalation phase to exhalation phase may take place in any one of the following cycling modes:

a. Time Cycled. The time at which changeover occurs may be controlled with the inhalation time control.

b. Volume Cycled. If the inhalation time control is preset, the tidal volume at which changeover occurs may be controlled with the flow rate control.

c. Pressure Cycled. Pressure cycling will occur if the maximum pressure control is set below the maximum pressure that would occur at the patient's mouth during time cycling.

d. Patient Cycled. Patient resists to the extent that pressure in the mouth exceeds the setting of the maximum pressure control. In this case, pressure cycling occurs as in part (c) above.

During exhalation phase, a constant pressure generator is connected to the patient. Two possibilities exist:

a. Constant atmospheric pressure generator - i.e., simple connection of patient to ambient through a non-rebreathing valve.

b. Constant positive pressure generator, or as it is sometimes called Positive End Exhalation Pressure (PEEP) generator. This may be approximated by a device which attempts to hold the pressure in the patient's mouth nearly constant regardless of flow rate during exhalation, but without introducing an undesirable retard effect (additional exhalation circuit resistance).

The changeover from exhalation phase to inhalation phase may take place in one of the following two modes:

a. Time Cycled. Controlled with the exhalation time control unless overridden by a patient inspiratory effort.

b. Patient Cycled. Changeover occurs when patient makes an inspiratory effort (level controlled by sensitivity setting).

The device also features an alarm to indicate disconnection or a substantial leak between the device and the patient. This alarm is either visible or audible or both.

The ventilator may be constructed completely of fluidic elements, all of which are conventional, off the shelf items, so that they are of reliable manufacture and operation, are well-known in the art and require no further description. Implementation of the basic control circuitry is not limited to fluidics, but it is believed that fluidic implementation offers the maximum possible simplicity, reliability, and ease of maintenance.

BRIEF DESCRIPTION OF THE DRAWINGS

These and other objects of this invention and a better understanding of the principles and details of the invention will be evident from the following description taken in conjunction with the appended drawings, in which:

FIG. 1 shows in schematic form the fluidic system of this invention.

FIG. 2 shows the relationship between PEEP output pressure $P_U$, and the difference between patient pressure $P_I$ and constant pressure $P_T$.

DESCRIPTION OF THE PREFERRED EMBODIMENT

This invention relates to the design of a ventilator which can operate on time cycle or pressure cycle or patient cycle or any combination of the three. The device can be used either in the control mode or in the assist-control mode. During the control mode of operation, the patient ventilation is entirely controlled by the machine. In the assist-control mode the change from the exhalation phase to inhalation phase occurs when the patient makes an inspiratory effort. The assist-control mode includes a safety feature of initiating an inhalation phase after a preset exhalation time if the patient fails to initiate the inhalation phase. In both control modes, and during operation, a safety feature is provided to limit the maximum pressure in the mouth of the patient during the inhalation phase.

Referring now to the drawing, a principal part of the ventilator is indicated generally by numeral 10. This is the time control portion of the apparatus which controls the operation of a breathing gas or pilot operated, or main control, or on-off valve system indicated generally by numeral 11 which provides breathing gas through a control needle valve R5 at constant flow rate to the patient. There is a maximum pressure control indicated generally by the numeral 12 which serves to initiate the exhalation portion of the cycle in the event that the gas pressure at the patient's mouth exceeds a preset level. There is an assist control indicated generally by the numeral 14 which monitors the pressure at the patient's mouth and starts the inhalation portion of the cycle whenever the patient generates a pressure lower than the difference between the output pressure ($P_Z$) of a positive pressure of end exhalation pressure (PEEP) circuit and a pre-set reference pressure ($P_R$). There is a PEEP control indicated by the numeral 53 which holds a preset positive pressure in the patient's lungs at the end of exhalation. There is a manual control indicated by the numeral 60 which allows the initiation of the inhalation phase at any time during the exhalation phase. There is a disconnect alarm indicated generally by the numeral 16 which operates an alarm whenever the breathing apparatus is disconnected from the patient, or there is a substantial leak in the patient circuit.

A source of breathing gas indicated by the designation T2 goes by way of pressure regulator 38 through a pilot operated valve 40, a constant flow rate control valve or adjustable resistance R5 and a non-rebreathing valve 55 to the patient. For a given setting of the flow rate control valve R5, the mass flow rate delivered to the patient during the inhalation phase is constant, and is independent of the patient's conditions. Reference is made to "Compressible Fluid Flow," by Ascher H. Shapiro, The Ronald Press Co., New York, New York 1953, pages 84-90. The pressure in the mouth of the patient, that is, at 70, the junction of the non-rebreathing valve 55 and the patient, is the pressure signal I. There are four auxiliary controls which are responsive to this pressure signal I.

The source T1 of control fluid, through pressure regulators 36 and 58 serves to operate the fluidic circuits. This source can be any suitable gas, or mixture of gases. The pressure regulator 58 controls the supply pressure S to all fluidic elements except TDR1 and TDR2, which are controlled by the pressure regulator 36. TDR1 has a time delay control which is comprised of a variable flow resistance element R1. Similarly, TDR2 has an independent time delay control comprising variable flow resistance R2. There is an E input to TDR1 and an F input to TDR2. These inputs are derived from a bistable means, such as flip flop FF1 32. The E and F outputs of the FF1 go to the TDR1 and TDR2 and also go as inputs to a digital amplifier 34, an output of which, G, goes to the main control valve 11. When there is pressure on G the valve 40 opens and breathing gas flows from T2 through the flow rate control valve R5, and non-rebreathing valve 55 to the patient. TDR1 has an A output and TDR2 has a B output. These two outputs A and B go to flip flop FF1 indicated by numeral 32 and are the primary inputs. They operate the FF1 in the cycle set by the time delays provided by the TDR1 and TDR2 circuits.

Consider that there is an operation of the TDR1 (initiation of inhalation phase) and output A has a logical one momentarily, which means that it has pressure. This pressure pulse at input A on the FF1 causes the output F to assume a logical one, the output E to assume a logical zero, and the TDR1 to be reset. The logical one output of F going to the TDR2 initiates a time delay set by the control R2 which corresponds to the inhalation time. The pressure on the output F goes also to the input of the digital amplifier 34 and causes the G output to have a logical one, and to apply pressure to the valve 40, causing it to open. This is the start of the inhalation phase. After the time delay set by R2 the pressure at the B output of TDR2 changes from a logical zero to a logical one momentarily. This pressure pulse applied to FF1 causes it to switch so that output E is a logical one, output F is logical zero, and TDR2 is reset. The logical one output on E going to TDR1 initiates the time delay set by R1 which corresponds to the exhalation time. The logical one E output of FF1 also causes the digital amplifier 34 to switch the G output from a logical one to a logical zero, which permits the valve 40 to close, thus initiating the start of the exhalation phase. The cycle continues to repeat itself. The actual on and off time of the two time delay relays 28, 30 can be set independently of all factors.

The time delays provided by the TDR1 and TDR2 circuits can be controlled by another method. In this method, the resistances R1 and R2 are set at some predetermined values which set a particular ratio of inhalation time to exhalation time, (I/E) ratio, and the frequency of cycling is then varied by varying the supply pressures to the two time delay relays by means of the pressure regulator 36. Thus the system can operate on a time of inhalation and a time of exhalation (first method) or it can be operated on an inhalation/exhalation ratio and frequency (second method). With both of these methods the patient can be adequately ventilated under different conditions.

The patient is connected to the machine via a breathing hose 71 and a non-breathing valve 55. During inhalation, the signal G from flip flop FF1 32 causes the monostable means such as OR gate 57 to switch, making the output signal G1 to be a logical one. The signal G1 applies pressure at the input V of pilot-operated valve 55, causing it to close. The patient then receives the breathing gas through valves 40 and R5. During exhalation, the signal G1 will be zero, valve 40 closes, valve 55 opens, and the patient can exhale through the valve 55. The pressure at the end of exhalation may be either atmospheric or higher depending on the setting of the PEEP control which is discussed later.

There is a maximum pressure control indicated generally by the numeral 12. This comprises a Schmitt trigger 44 labeled ST1 which has two inputs, an I input and a Q input. There is a D output. The pressure signal I from the patient at junction 70 goes as input to the ST1 via line 72. The Q input is a pressure set by a variable resistance R4. The Schmitt trigger 44 is controlled by the opposition of the gas pressure at the I and Q inputs. The Q input is set at a desired value above the normal I input. When the pressure at the I input exceeds this preselected value, it causes the ST1 44 to switch the D output to a logical one. This applies pressure at the D input to the FF1 32. This D input is a second input, in parallel with the B input, and causes the FF1 to be switched to provide a logical one at the E output which causes the exhalation phase to begin.

It must be noted that the maximum pressure control may be used to intentionally pressure cycle the ventilator. With proper setting of the inhalation time, flow rate control, and the maximum pressure control, the inhalation phase may be terminated when the patient pressure reaches a desired value. The exhalation phase may be either timed by the TDR1 circuit or controlled by the patient.

There is a second feature which is used when the instrument is called upon to assist the patient in breathing. When the patient through inspiratory effort causes the pressure at I to be reduced sufficiently, the inhalation phase will be initiated. The Schmitt trigger ST2 indicated generally by the numeral 14, senses this reduced pressure and provides a correction. The ST2 has an I input, an R input, and a Z input. The Z input is a pressure signal equal to the PEEP setting. The R input is a positive pressure controlled by a needle valve R3. The pressure signal at R normally over balances the differential pressure between the inputs at I and Z, and the output C is then a logical zero. When the input signal at I reduces, the differential pressure between inputs at I and Z will overcome the pressure at input R, and the C output of ST2 becomes a logical one and applies pressure to the C input of the flip flop FF1 32, causing it to switch, initiating the inhalation phase. In other words, a reduction of pressure on the I input in line 72 causes the valve 40 to open, which in turn directs breathing gas to the patient. It should be noted that the sensitivity control is independent of the PEEP setting because the switching of the Schmitt trigger ST2 depends only on the differential pressure between I and Z and not their absolute values.

To operate the ventilator as an assistor-controller, the exhalation time is set significantly longer than desired by the patient and the sensitivity is set sufficiently low so that the patient can initiate the inhalation phase. If for some reason the patient does not initiate the inhalation phase, automatic initiation will occur at the end of the time set by the exhalation time control. This is an inherent safety feature built into the circuit to prevent loss of cycling when patient is not able to initiate inhalation.

The positive end exhalation pressure (PEEP) control is indicated generally by the numeral 53. It consists of a proportional amplifier 54, labeled PA which has two inputs, I and T. There is an output U connected to port V of valve 55 through a restrictor R8. A reference bias pressure is introduced at T through a variable resistor or needle valve R6. FIG. 2 shows the plot of the pressure at U versus the differential pressure between I and T. The operation of the PEEP control is explained using the following example.

Assume that the bias pressure $P_T$ at T is set such that point 1 in FIG. 2 represents the output pressure at port U ($P_U$) of the proportional amplifier 54 at the end of exhalation. During inhalation, the valve 40 is open and valve 55 is closed, and breathing gas is delivered to the patient. The patient pressure $P_I$ will increase during inhalation and hence the pressure $P_U$ will increase (say it reaches Point 2 at the end of inhalation). At the end of inhalation, the signal from the port G of the digital amplifier will become a logical zero, and the force due to the spring and the patient pressure acting on one side of valve 55 will overcome the force due to the pressure acting on port V, thus opening the valve. So the patient will exhale. The exhalation will continue until the patient pressure decreases to a level at which the force acting on port V is sufficient to close the valve 55. Since the spring force is very small, the force due to $P_V$ is mainly balanced by the force due to the patient pressure. Hence different back pressures (PEEP) can be achieved by different settings of $P_V$ through the resistor R6.

The ventilator circuit shown in FIG. 1 can also operate in the intermittent mandatory ventilation (IMV) mode. In this mode the resistance R2 of TDR2 is set to obtain a desired inhalation time for the mandatory breath. The resistance R1 of TDR1 is then adjusted to a particular exhalation time which will yield a desired rate for IMV. The tidal volume for the mandatory breath may be obtained using the flow rate control R5. The operation of the time control portion of the apparatus has been explained earlier.

The output signal G of the digital amplifier 34 is off for duration of the exhalation time set by resistor R1. During this time, the valve 40 is closed and the signal at input V of valve 55 is off. The spring force acting on valve 55 will open the valve thus connecting the patient to atmosphere. Hence the patient can breathe atmospheric air mandatory through valve 55 between spontaneous breaths.

There is a safety feature of this device which is indicated generally by the numeral 16. This is a warning signal (visual or audible) to indicate when the gas line 71 from the ventilator to the patient has been disconnected or has developed a substantial leak, i.e. the patient is not receiving gas in accordance with the control settings.

The sensor for this condition is a diaphragm valve 18 which has the pressure $P_I$ on one side. So long as the patient is connected to the device the pressure $P_I$ will build up during the inhalation phase and the valve 18 will be closed. However, if the patient becomes disconnected, the pressure $P_I$ will not reach the normal level during the inhalation phase, and the valve 18 will remain open.

When the valve 18 is closed, a back pressure is built up in line 48 connected to the back pressure switch (BPS) 20. The line 48 is connected to the supply port S of BPS 20 through a fixed resistor 50. When the valve 18 is open, there is no back pressure built up in line 48. However, when the valve 18 closes a pressure will build up in the line 48 and at the input 0 of the BPS 20. This will cause the L output to switch to a logical one. This is communicated to the L input of a second bistable means such as FF2 (flip flop) 22. The other input side of the FF2 22 is connected to the G output of the digital amplifier 34 through a resistor R7.

During the inhalation phase, the output G of DA 34 is a logical one. This pressure signal, applied at input port G of a monostable means such as NOR 24 and at input port P of FF2 22, causes these two elements to switch making output X of NOR 24 and output W of FF2 22 equal to logical one. If the connection between the patient and the ventilator is normal, patient pressure $P_I$ builds up during the inhalation phase and closes valve 18. The closing of valve 18 causes a pressure signal to be applied at input port O of BPS 20 making the output L a logical one. The output L of BPS 20 is applied at input port L of FF2 22. The pressure $P_L$ at input port L is larger in magnitude than the pressure $P_P$ at input port P (because of the resistance R7). This causes FF2 22 to switch making output W logical zero and output K logical one. The output K of FF2 22 is applied at input K of NOR 24. This input along with the input at G keeps NOR 24 switched making output X a logical one and output Y a logical zero (i.e., no alarm).

During the exhalation phase, the output G of DA 34 is a logical zero. Hence, there is no pressure signal applied at either port G of NOR 24 or port P of FF2 22. As the patient exhales the pressure $P_I$ decreases, and thus opens valve 18. This causes BPS 20 to switch making output L a logical zero and output J a logical one. Hence, during exhalation the pressure signal at input L of FF2 22 is zero. However, the output K of FF2 22 continues to be a logical one since no reset signal is applied at input port P. The output at port K keeps the NOR 24 in the switched state making output X a logical one and output Y a logical zero (i.e., no alarm).

If there is either a disconnection between the patient and the ventilator or if there is a substantial leak in the patient circuit, the patient pressure $P_I$ does not reach the normal value during the inhalation phase, and valve 18 remains open. Hence, no pressure signal is applied at input port 0 of BPS 20 during inhalation phase and the output L remains a logical zero. The FF2 22 continues in the reset condition with output W a logical one and output K a logical zero. The pressure at input G switches NOR 24 making output X a logical one and output Y a logical zero. However, during the exhalation phase, the pressure signals at both the inputs G and K of NOR 24 are zero and hence the output X will be a logical zero and output Y will be a logical one indicating the disconnection. The alarm is intermittent, off during the inhalation phase and on during the exhalation phase.

There is a provision for manually triggering the inspiration cycle. This is done by pressing the push button PB, indicated by numeral 60, which will apply an input pressure at A to the FF1 32. This results in output F being equal to a logical one, which initiates the inhalation phase. The inhalation phase is timed by the TDR2 circuit as explained earlier. Normal cycling will occur if PB 60 is not activated.

There is also a safety feature built into the unit in the event of failure of the source pressure T1. In such a case, the pressure signal at the input V of valve 55 will be zero and the spring force will cause the valve to open. The patient can breathe the atmospheric air through the valve 55.

The invention has been described in terms of generalized circuit elements, such as flip flops, Schmitt triggers, NOR gates, etc., all of which may be called fluidic devices. These are standardized devices for use in fluidic systems. A large number of manufacturers now supply these devices which are available from stock, and can be described by a catalog number. The detailed description can be provided by the manufacturer and need not be described in detail here.

Examples of these devices are as follows:

1. Breathing gas control valve part 11. Catalog #192621, Fluidic Products Dept., Corning Glass Works, Corning, New York 14830.

2. Time Delay Relay, parts 28 and 30. Catalog #191465, Corning, New York.

3. OR/NOR Gate, parts 24 and 57. Catalog #191445, Corning, New York.

4. Flip Flop, parts 22 and 32. Catalog #191446, Corning, New York.

5. Digital Amplifier, part 34. Catalog #191452, Corning, New York.

6. Schmitt Trigger, parts 44 and 46. Catalog #192954, Corning, New York.

7. Back Pressure Switch, part 20. Catalog #191479, Corning, New York.

8. Proportional Amplifier, part 54, Catalog #191711, Corning, New York.

9. Push Button, part 60, Catalog #192496, Corning, New York.

10. Visual Indicator, part 26, Catalog #191817, Corning, New York.

11. Pressure Regulators, parts 36, 38 and 58, Catalog #191481, Corning, New York.

The non-rebreathing valve 55 has been mentioned at a number of places in the preceding description. This is a standard piece of apparatus which is available off the shelf, and is well-known to a man skilled in the art, and need not be illustrated. A brief description will suffice.

The conventional non-rebreathing valve consists of a passage, one end connected to the ventilator at point 70, the other end connected to a tube to the patient. There is a side opening in the passage connected to the atmosphere. This side opening is covered by a poppet valve which is controlled by a diaphragm and opposed by a spring. When the pressure $P_I$ on the diaphragm is high enough to overcome the force of the spring the poppet valve is closed.

During the inhalation phase, the diaphragm is inflated, forcing the poppet closed against the spring force. The gas from the ventilator passes through the passage to the patient. During exhalation the diaphragm is deflated, and the spring pushes the poppet open, and the patient can breathe out to the atmosphere.

The valve is so designed that when the poppet is off the seat, the resistance to the flow of gas through the valve is minimal. Hence, when the diaphragm is not inflated, the patient can breathe spontaneously through the valve.

While the invention has been described with a certain degree of particularity, it is manifest that many changes may be made in details of construction and the arrangement of components. It is understood that the invention is not to be limited to the specific embodiment set forth herein by way of exemplifying the invention, but the invention is to be limited only by the scope of the attached claim or claims, including the full range of equivalency to which each element or step thereof is entitled.

What is claimed is:

1. A positive pressure ventilator comprising:
   a. a source of breathing gas;
   b. a normally closed first valve means (40) for directing the breathing gas from said source to the patient;
   c. A first bistable means (32) for controlling said first valve means, said first bistable means having a first set of opposed control inputs;
   d. a first time delay means (28), and a second time delay means (30), each independently adjustable in time delay;
   e. means responsive to said first time delay means to operate one of said first inputs of said first bistable means to open said first valve means, and to trip said second time delay means, and to initiate the inhalation action; and
   f. means responsive to the operation of said second time delay means to operate a second one of said first inputs of said first bistable means to close said first valve means and to trip said first time delay means and initiate the exhalation action; and including
   g. between said source of breathing gas and said first valve means a pressure controller (38) for maintaining a constant supply pressure to said valve; and
   h. between said first valve means and said patient a flow rate control valve (R5);
   whereby a selected constant value of flow rate of gas is supplied to said patient when said first valve means is open; and including
   non-rebreathing valve means having an open and a closed position, including
   i. spring means to open said non-rebreathing valve in the absence of operating pressure, said non-rebreathing valve connected to the supply line of breathing gas for the patient and including
   j. fluidic OR gate means for applying pressure to close said non-rebreathing valve during the inhalation phase, and to open said non-rebreathing valve during the exhalation phase.

2. The ventilator as in claim 1, in which said first bistable means comprises a first fluidic flip flop means.

3. The ventilator as in claim 1 in which said first and second time delay means comprise fluidic time delay relays.

4. The ventilator as in claim 1, including:
   a first Schmitt trigger means 44 responsive to the pressure of the breathing gas to the patient for controlling said first bistable means through one of said second inputs to terminate said inhalation action and initiate said exhalation action.

5. The ventilator as in claim 1, including:
   a second Schmitt trigger means (46) responsive to the patient's inspiratory pressure, and means to control said first bistable means through a second one of said second inputs so as to terminate said exhalation action and initiate said inhalation action.

6. The ventilator as in claim 1, including:
   digital fluid amplifier means responsive to said first bistable means to control said first valve.

7. The ventilator as in claim 1, including:
   pressure control means applied to said first and second time delay means to control the frequency of the breathing cycle.

8. The ventilator as in claim 1, including:
   means responsive to the pressure in the breathing gas line to the patient for activating an alarm when the patient pressure is less than a selected value.

9. The ventilator as in claim 8 in which said means comprises:
   a. diaphragm valve means responsive to said patient pressure;
   b. back pressure switch means responsive to said diaphragm valve means;
   c. second bistable means responsive to said back pressure switch means;
   d. first monostable means responsive to said second bistable means; and
   e. alarm means responsive to said first monostable means.

10. The ventilator as in claim 1, including:
    a. first Schmitt trigger means (12) having an I input and a Q input and N and D outputs;
    b. an adjustable fluid pressure on said Q input;
    c. the I input controlled by the breathing gas pressure at the patient;
    d. said D output connected to a D input on said first bistable means parallel to said B input;
    whereby when said I pressure reaches a preselected value, said first Schmitt trigger will provide fluid pressure from said D output to said D input on said first bistable means to close said first valve, and initiate the exhalation phase of the breathing cycle.

11. The ventilator as in claim 1, including:
    a. second Schmitt trigger means having an I input, a Z input, and an R input, and C and M outputs;
    b. an adjustable fluid pressure on said R input;
    c. the I input controlled by the breathing gas pressure $P_I$ at the patient;
    d. said C output connected to a C input on said first bistable means parallel to said A input;
    whereby when said $P_I$ reaches a preselected negative value, said second C output of said Schmitt trigger is applied to said C input on said first bistable means to open said first valve and initiate the inhalation phase. a closed position, including
    spring means to open said valve in the absence of operating pressure, said valve connected to the supply line of breathing gas for the patient, and including
    second monostable means for applying pressure to close said valve during the inhalation phase, and to open said valve during the exhalation phase.

12. The ventilator as in claim 1, including:
    means for opening said non-rebreathing valve whenever the fluidic pressure fails;
    whereby the patient is connected to the atmosphere, and can breathe atmospheric air.

13. The ventilator as in claim 1, including:
    proportional amplifier means responsive to the end exhalation pressure in the patient's mouth to maintain said non-rebreathing valve closed until said mouth pressure exceeds a preselected value.

14. The ventilator as in claim 1 including:
    a manual control push button connected to said input A of said first flip flop to initiate the inhalation phase.

15. The ventilator as in claim 1, including:
    an intermittent mandatory mode of operation whereby a mandatory breath may be delivered to the patient at a controlled rate, and the patient may breathe atmospheric air spontaneously between mandatory breaths.

16. A positive pressure ventilator comprising:
a. a source of breathing gas;
b. a normally closed first valve means for directing the breathing gas from said source to the patient;
c. a first bistable means for controlling said first valve means, said first bistable means having a first set of opposed control inputs;
d. a first and a second time delay means, each independently adjustable in time delay;
e. means responsive to said first time delay means to operate one of said first inputs of said first bistable means to open said first valve means, and to trip said second time delay means, and to initiate the inhalation action;
f. means responsive to the operation of said second time delay means to operate a second one of said first inputs of said first bistable means to close said first valve means and to trip said first time delay means and initiate the exhalation action; and further including
g. diaphragm valve means responsive to the patient pressure, said patient pressure being positive, and of sufficient magnitude during the inhalation phase to close said diaphragm valve means;
a second bistable means having a set of opposed control inputs back pressure switch means responsive to the closing of said diaphragm valve means to apply fluid pressure to a first input of a second bistable means, a second input to said second bistable means connected through a resistance to the output of a digital amplifier responsive to said first bistable means, an output of said second bistable means connected to a first input of a first monostable means, a second input of said first monostable means connected to said output of said digital amplifier, the pressure on said first input keeping the output of said first monostable means a logical zero; and
i. alarm means responsive to a logical one on said output of said first monostable means;
whereby when the patient is disconnected from said breathing apparatus, said patient pressure never gets high enough to close said diaphragm valve, whereby said back pressure switch never operates and said second input resets said second bistable means, taking said pressure at said first input off of said first monostable means and permitting output of said first monostable means to change to a logical one and activate an alarm.

17. A positive pressure ventilator comprising;
a. a source of breathing gas;
b. a normally closed first valve means (40) for directing the breathing gas from said source to the patient;
c. a first bistable means (32) for controlling said first valve means, said first bistable means having a first set of opposed control inputs;
d. a first time delay means (28), and a second time delay means (30), each independently adjustable in time delay;
e. means responsive to said first time delay means to operate one of said first inputs of said first bistable means to open said first valve means, and to trip said second time delay means, and to initiate the inhalation action; and
f. means responsive to the operation of said second time delay means to operate a second one of said first inputs of said first bistable means to close said first valve means and to trip said first time delay means and initiate the exhalation action; and including
g. between said source of breathing gas and said first valve means a pressure controller (38) for maintaining a constant supply pressure to said valve; and
h. between said first valve means and said patient a flow rate control valve (R5);
whereby a selected constant value of flow rate of gas is supplied to said patient when said first valve means is open; and including
means responsive to the pressure in the breathing gas line to the patient for activating an alarm when the patient pressure is less than a selected value during said inhalation action, comprising;
i. diaphragm valve means responsive to said patient pressure;
j. back pressure switch means responsive to said diaphragm valve means;
k. second bistable means responsive to said back pressure switch means;
l. fluidic NOR gate means responsive to said second bistable means and
m. alarm means responsive to said fluidic NOR gate means.

18. The ventilator as in claim 17, including:
non-rebreathing valve means having an open and a closed position, including
spring means to open said valve in the absence of operating pressure, said valve connected to the supply line of breathing gas for the patient, and including
second monostable means for applying pressure to close said valve during the inhalation phase, and to open said valve during the exhalation phase.

19. The ventilator as in claim 17, in which said second bistable means comprises a second fluid flip flop means.

* * * * *